United States Patent [19]

Schleppinghoff et al.

[11] Patent Number: 4,804,704
[45] Date of Patent: Feb. 14, 1989

[54] CROSSLINKED ORGANIC RESINS CONTAINING SIO₂ AND SULPHONIC ACID GROUPS

[75] Inventors: Bernhard Schleppinghoff, Dormagen; Mathias Lux; Horst Reinhardt, both of Bergheim, all of Fed. Rep. of Germany

[73] Assignee: EC Erdolchemie GmbH, Cologne, Fed. Rep. of Germany

[21] Appl. No.: 24,209

[22] Filed: Mar. 10, 1987

[30] Foreign Application Priority Data

Mar. 29, 1986 [DE] Fed. Rep. of Germany ....... 3610705

[51] Int. Cl.⁴ .............................. C08K 3/34; C08K 3/36
[52] U.S. Cl. .................................... 524/549; 525/442; 524/575; 524/594
[58] Field of Search ............................ 525/333.5, 442; 524/547, 549, 575, 594

[56] References Cited

U.S. PATENT DOCUMENTS 2,578,937 12/1951 Kunin ................................ 525/333.5
4,125,506 11/1978 Lundberg ............................ 524/547
4,286,082 8/1981 Tsubakimoto ....................... 526/240

Primary Examiner—Christopher Henderson
Attorney, Agent, or Firm—Sprung Horn Kramer & Woods

[57] ABSTRACT

Crosslinked organic resins, containing SiO₂ and sulphonic acid groups, having an SiO₂ content of 0.1–10% by weight, relative to the total weight of the SiO₂-containing resins, are prepared by steeping crosslinked organic resins, containing sulphonic acid groups, in the alkali form in aqueous alkali metal silicate solutions or (quaternary) alkylammonium silicate solutions, and subsequently precipitating the SiO₂ using mineral acid, and simultaneously converting the resin into the H⁺ form. These resins can be used as acid catalysts in the cleavage of tert.-alkyl ethers into the basic tertiary olefins and the basic alkanols. This use has proven particularly advantageous when the tert.-alkyl alkyl ethers to be cleaved are employed together with water for the cleavage.

9 Claims, 1 Drawing Sheet

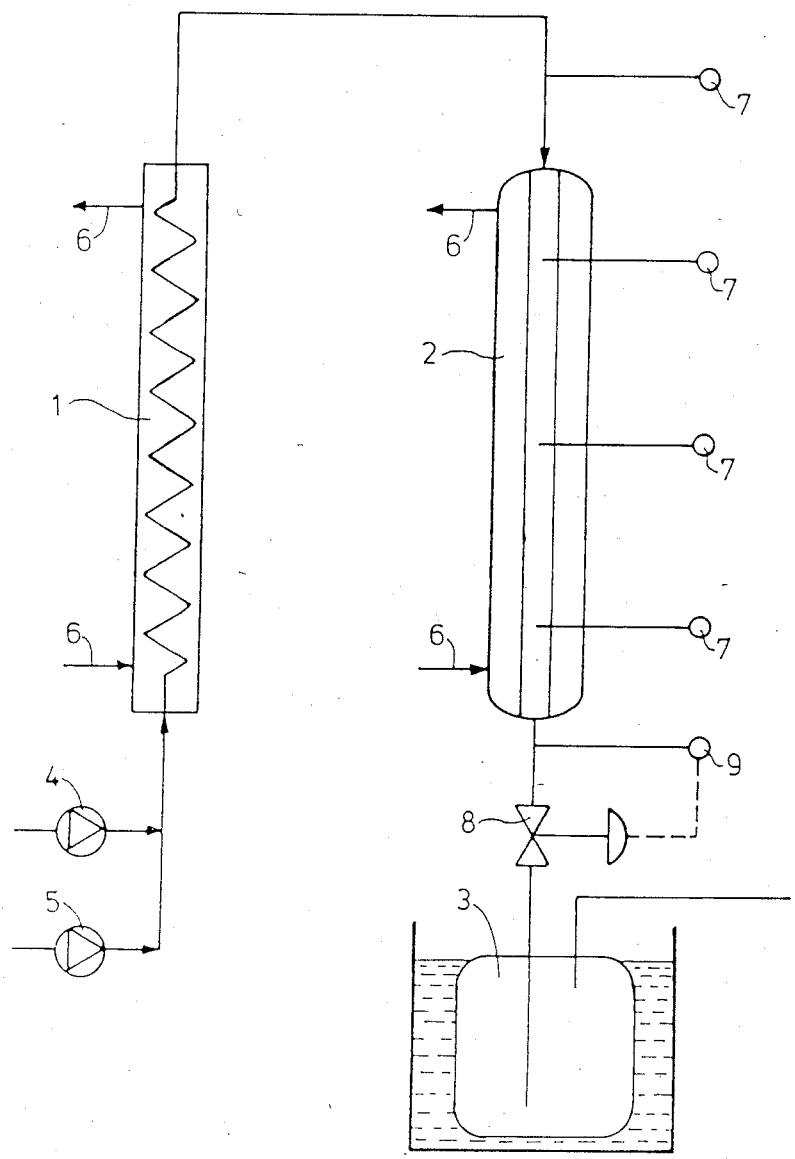

CROSSLINKED ORGANIC RESINS CONTAINING SIO₂ AND SULPHONIC ACID GROUPS

The present invention relates to crosslinked organic resins which are characterized in that they simultaneously contain $SiO_2$ and sulphonic acid groups, a process for the preparation thereof, and the use thereof for the cleavage of tert.-alkyl alkyl ethers into the basic tertiary olefins and alkanols.

New crosslinked organic resins containing sulphonic acid groups have been found which are characterized in that they contain 0.1–10% by weight of $SiO_2$, relative to the total weight of the $SiO_2$-containing resins.

The new resins are based on strongly acidic cation exchange resins. These may be all known types, such as, for example, sulphonated phenol-formaldehyde resins, sulphonated coumarone-indene condensation products, sulphonated styrene-divinylbenzene resins, preferably the last-mentioned sulphonated styrene-divinylbenzene resins. Such resins have a crosslinking (content of crosslinking agent, such as divinylbenzene) of 2–65%, preferably 8–25%.

The new resins have an $SiO_2$ content of 0.1–10% by weight, preferably 0.3–3% by weight, relative to the total weight of the new $SiO_2$-containing resins.

The new $SiO_2$-containing resins can be prepared by steeping a crosslinked organic resin, containing sulphonic acid groups, in its alkali form in aqueous alkali metal silicate solution or (quaternary) alkylammonium silicate solution, and subsequently precipitating the $SiO_2$ using mineral acid with simultaneous conversion of the resin into the $H^+$ form.

Where a higher $SiO_2$ content is desired, the steeping and the subsequent precipitation of $SiO_2$ can be repeated several times. If the $SiO_2$ content is to be set with greater accuracy, such repeated steeping and precipitation is the preferred method of preparation.

The invention furthermore relates to a process for the preparation of crosslinked organic resins containing $SiO_2$ and sulphonic acid groups, which is characterized in that crosslinked organic resins, containing sulphonic acid groups, in the alkali form are steeped in a first step in aqueous alkali metal silicate solution or (quaternary) alkylammonium silicate solutions and the steeped resins are treated with mineral acids in a second step in order to precipitate $SiO_2$ and simultaneously convert to the $H^+$ form, and, if appropriate after conversion of the resins into the alkali form, the steeping and precipitation steps are repeated.

The abovementioned resins, containing sulphonic acid groups, which are known as cation exchangers are initially converted into the alkali form, for example using an aqueous solution of an alkali metal hydroxide or of a simple alkali metal salt, in order to carry out the process according to the invention. This working procedure is well-known to those skilled in the art from ion exchanger technology.

The cation exchanger, moist with water, in the alkali form is then treated with an aqueous alkali metal silicate solution (waterglass solution), such as sodium waterglass or potassium waterglass, or an aqueous (quaternary) alkylammonium silicate solution. The silicate concentration in the waterglass solution is 1–20% by weight, preferably 5–15% by weight, relative to the total weight of the aqueous silicate solution. If alkylammonium silicate solutions are employed, the quaternary alkylammonium solutions are preferred. (Quaternary) alkylammonium cations are known to those skilled in the art.

The silicate solution is allowed to act on the cation exchanger for 1–1,000 hours, preferably 50–200 hours.

After separating off the cation exchanger from the excess silicate solution, it is treated with diluted mineral acid, such as sulphuric acid, hydrochloric acid, phosphoric acid or nitric acid, preferably sulphuric acid or hydrochloric acid. During this treatment, $SiO_2$ is precipitated and the cation exchanger is simultaneously converted into the $H^+$ form. The concentration of the mineral acid is not critical; it is frequently in the range 2–10% by weight.

The $SiO_2$-containing cation exchanger is subsequently washed until neutral and can be employed, for example, in this water-containing form. However, it is furthermore possible to displace the water by methanol after the neutral washing. The $SiO_2$-containing cation exchangers according to the invention may also be employed in this methanol-moist form; however, it is also furthermore conceivable for the methanol to be removed, for example by drying at somewhat elevated temperature in vacuo, so that the $SiO_2$-containing cation exchangers may also be used in dry form.

In order to increase the proportion of $SiO_2$ or for more precise setting of a certain desired proportion of $SiO_2$, the steeping and precipitation of $SiO_2$ can also be repeated several times, if desired.

A variant of the described preparation process for the new resins comrises initially allowing the resins, in the alkali form, to pre-swell in a polar, water-miscible solvent and only then carrying out treatment with the aqueous silicate solution. A further variant comprises allowing the polar, water-miscible solvent and the aqueous silicate solution to act simultaneously. Suitable polar, water-miscible solvents are, for example, polyhydric alcohols, such as glycol and glycerol, acetone, methyl ethyl ketone and others. Polyhydric alcohols, particularly glycol, are preferred.

The silicate solution is frequently allowed to act at temperatures of 293–303 K., but can certainly be allowed to act in the temperature range 283–373 K.

The $SiO_2$-containing resins according to the invention are excellently suited as acid catalysts for cleavage of tert.-alkyl alkyl ethers into the basic tertiary olefins and alkanols. The invention thus furthermore relates to this use of the new crosslinked organic resins, according to the invention, containing $SiO_2$ and sulphonic acid groups.

Tertiary olefins are important precursors for oligomers, for example for solvents and lubricants, for polymers and copolymers, and for higher grade chemicals, such as pinacolin, neocarboxylic acids, isoprene inter alia.

Tertiary olefins arrive in crude form, for example in the thermal or catalytic cracking of light petroleum, naphtha and other suitable starting materials or on the dehydrogenation and/or isomerization thereof; they usually exist here as a mixture with a large number of saturated and unsaturated attendant materials whose distillative separation is difficult and expensive since it starts from distillation cuts in which mixture components of similar boiling point and with the same or a similar number of C atoms are present.

The tertiary olefins are thus isolated via selective reaction, separation of the reaction product and decomposition of the separated pure reaction products. Whereas the selective esterification using sulphuric acid and decomposition of the esters formed was used previously, in recent times the selective etherification of the tertiary olefins using alkanols on acid cation exchangers is preferred in order to avoid corrosive sulphuric acid. The tert.-alkyl alkyl ethers formed may be separated off from the materials accompanying the tertiary olefins by known methods (distillation, azeotropic distillation, extractive distillation inter alia) and obtained in pure form.

The tert.-alkyl alkyl ethers may be cleaved into the basic tertiary olefins and alkanols; the separation of the tertiary olefins thus prepared presents no difficulties. The cleavage is carried out on suitable catalysts at temperatures which are higher than the temperatures required for the formation of the ethers.

Mineral catalysts, such as silicic acids or aluminium oxides having large surface areas, silico-aluminates, mordenites, zeolites, oxides of other elements, phosphoric acid or salts which react in an acidic fashion were hitherto frequently used as catalysts for the ether cleavage. These mineral catalysts are operated at elevated temperatures up to 673 K. Undesired byproducts, particularly dialkyl ethers, occur during this from the alkanols produced during the cleavage. This formation of dialkyl ethers increases to a greater extent with increasing temperature and thus removes alkanol from the overall ether formation/ether cleavage process, the alkanol thus needing to be replaced again; furthermore, the work-up becomes more complicated due to the formation of byproducts. On the other hand, the danger of hydration of the tertiary olefin to be obtained (formation of the corresponding tert.-alkanols) becomes greater due to the water produced during the ether formation, whereby losses of the desired tertiary olefins arise or a downstream dehydration must be carried out. The undesired formation of dialkyl ethers cannot be suppressed by reducing the reaction temperature since the mineral catalysts mentioned then lose their efficacy too strongly.

In spite of the danger of hydration of the tertiary olefins produced, an attempt has thus been made to carry out the cleavage of ether on mineral catalysts in the presence of water in order to control the undesired formation of dialkyl ethers (GB No. 1,176,620; DE-OS (German Published Specification) No. 3,142,461).

It has furthermore been proposed that the cleavage of ether be carried out on acid cation exchangers (DE-AS (German Published Specification) No. 1,216,865; U.S. Pat. No. 4,447,668). However, it is also impossible here to suppress the formation of dialkyl ethers.

A general difficulty of all ether cleavage processes is that this reaction is endothermic and can thus only be carried out in a satisfactory fashion with supply of heat. On the other hand, the cation exchangers, as organic materials, only have a limited thermal stability, so that the supply of heat of reaction by increasing the temperature is not possible to any desired extent.

The use according to the invention of the new $SiO_2$-containing resins, described above, as catalysts for the cleavage of tert.-alkyl alkyl ethers now simultaneously brings the advantages of suppressing the formation of dialkyl ethers, the suppression of oligomers of tertiary olefins and the suppression of the hydration thereof to form the corresponding tertiary alkanols. With respect to the tertiary alkanols, it has even been observed that tertiary alkanols which are contained as an impurity in the starting material are even partially dehydrated to form tertiary olefins.

As tert.-alkyl alkyl ethers for the cleavage of the $SiO_2$-containing resins according to the invention, those may be mentioned, for example, which are based on primary alcohols having 1–4C atoms, such as methanol, ethanol, n-propanol, n-butanol, preferably methanol or ethanol, and tertiary olefins having 4–7C atoms, such as i-butene, i-amylenes, i-hexenes, i-heptenes, preferably i-butene and i-amylenes. Such ethers are, for example, methyl tert.-butyl ether (MBTE), ethyl tert-butyl ether, propyl tert.-butyl ether, n-butyl tert.-butyl ether, tert.-amyl methyl ether (TAME), tert.-amyl-ethyl ether, tert.-amyl propyl ether, tert.-amyl n-butyl ether, methyl tert.-hexyl ether and methyl tert.-heptyl ether.

The cleavage of ether on the new resins according to the invention may be carried out, for example, at temperatures of 333–400 K., preferably 353–393 K., at a reaction pressure of 1–50 bar, preferably 1–10 bar, particularly preferably 1–3 bar, and a WHSV (Weight Hourly Space Velocity) of 1–50 kg of starting material per hour and per liter of catalyst, preferably at 2–20, particularly preferably at 3–10 kg/h.l of catalyst. The reaction can be carried out both in the liquid and also in the gaseous phase, but preferably in the gaseous phase.

The tubes containing the catalyst can possess, for example, ribs pointing inwardly. The catalyst can furthermore be arranged in the catalyst bed alternatingly with layers of inert materials, such as steel elements, $Al_2O_3$, ceramic elements etc. The entire catalyst bed can also comprise a mixture of the new resins as catalysts and one of the inert substances mentioned.

Due to the use of the new resins as catalysts, the ether cleavage can be carried out at relatively low temperatures, low pressures and high space velocities compared to the processes used hitherto, high cleavage conversions and high selectivities up to greater than 99% being achieved. The subsequent separation and purification of the tertiary olefins are thereby considerably simplified.

It has furthermore been found that, when using the new resins as catalysts in the cleavage of ether described, the efficacy of the latter can be further increased by adding water to the tert.-alkyl alkyl ether to be cleaved. In a surprising fashion, hydration of the tertiary olefins does not occur during this, and the suppression of the dialkyl ethers and of the oligomers of the tertiary olefins is also further increased. The amount of water added is 2–50% by weight, preferably 5–40% by weight, relative to the amount of the tert.-alkyl alkyl ether employed. In the case of the cleavage of tert.-amyl methyl ether, an amount of 5–20% by weight of water, relative to the amount of ether, has proven particularly favourable.

The process can be carried out both in the liquid and also in the gaseous phase, also when using water. In both cases, but particularly when working in the gaseous phase, heat of reaction can be introduced into the reaction space by the use, according to the invention, of steam, particularly if working in the gas phase and then the heat of condensation of the water is also available in addition to the sensible heat. A further advantage of the concomitant use of water in the cleavage of ether is that the condensed cleavage products can be separated better and more quickly into an organic phase, which contains the tertiary olefin, and an aqueous-alkanolic phase. By means of this, the separation of residual alkanol from the tertiary olefin is simplified or possibly completely dispensed with.

EXAMPLES

Example 1

(Preparation of an SiO$_2$-modified cation exchanger)

250 ml of sulphonated styrene-divinylbenzene resin (Lewatit SPC 118 from Bayer), damp with water, were placed in a glass tube of diameter 25 mm and a volume of about 500 ml, having a sealed-in glass frit, and were initially washed with methanol and subsequently with distilled water. The cation exchange resin, pre-purified in this fashion, was subsequently converted into the Na$^+$ form using 5 kg of a 4% strength sodium hydroxide solution, about 2 hours being necessary for this. After separating off the sodium hydroxide solution, the cation exchange resin was transferred into a sealed vessel together with 255 g of a 10% strength aqueous sodium silicate solution (sodium waterglass) and left there for 120 hours at about 25° C. After separating off the sodium silicate solution, the cation exchange resin was rinsed in the glass tube described above together with 250 ml of distilled water, subsequently converted into the H$^+$ form using 750 ml of a 4% strength hydrochloric acid, and washed with distilled water until neutral. The catalyst thus prepared can be employed for the following examples moist with water, moist with methanol or in a dried form. The SiO$_2$ content was 0.46% by weight.

Example 2

The following working procedure was carried out for the preparation of an SiO$_2$-modified cation exchanger in the presence of a polar, water-miscible solvent: the cation exchanger used in Example 1 was pretreated as in Example 1 with methanol, distilled water and sodium hydroxide solution. 250 ml of the cation exchanger thus pretreated were transferred into a sealed vessel together with 750 ml of a solution of 375 ml of monoethylene glycol and 375 ml of a 10% strength aqueous sodium silicate solution, and left there for 120 hours. After separating off the cation exchanger, this was rinsed with 250 ml of distilled water in the fashion described in Example 1 and converted into the H$^+$ form using 750 ml of a 4% strength hydrochloric acid, and subsequently washed with distilled water until neutral. This catalyst can also be used moist with water, moist with methanol or in dried form. The SiO$_2$ content was 1.4% by weight.

Examples 3-9

The apparatus represented in the FIGURE was used for carrying out the examples. In the FIGURE, (1) denotes a preheater or evaporator, (2) denotes a cleavage reactor which is filled with a strongly acidic cation exchanger, (3) denotes a cooled and de-aerated receiver, (4) denotes a laboratory pump as metering device for the tert.-alkyl alkyl ether to be cleaved, (5) denotes a laboratory pump as metering device for the water to be added, (6) denotes heat transfer streams, the temperature of which can be adjusted by means of thermostats, (7) denotes temperature measurement points, (8) denotes a pressure valve and (9) denotes a device, for measuring the reaction pressure, which acts on (8) via a control circuit. (2) is a stainless steel twin-jacket reactor having an internal diameter of 25 mm and a length of 350 mm. The reaction mixture condensed in (3) separated into two phases, which were separated from one another, weighed and analysed.

Examples 3, 4, 8 and 9 are comparison examples (resins without SiO$_2$), and Examples 5-7 are examples of the invention (resins, according to the invention, with SiO$_2$). In Examples 5 to 7, a SiO$_2$-modified cation exchanger according to Example 1 was employed, whereas a cation exchanger based on the SiO$_2$-modified cation exchanger prepared in Example 1 without this SiO$_2$ modification was employed in Examples 3, 4, 8 and 9.

The tert.-amyl methyl ether (TAME) to be cleaved, employed in Examples 3-9, had the following composition:

| | |
|---|---|
| tert.-amyl methyl ether (TAME) | 98.0% by weight |
| tert.-amyl alcohol (TAA) | 0.9% by weight |
| tertiary C$_7$ ethers | 0.5% by weight |
| methanol | 0.1% by weight |
| water | 0.1% by weight |
| benzene | 0.2% by weight |
| other hydrocarbons | 0.2% by weight. |

The following table contains the reaction conditions (pressure, temperature, catalyst, quantity feed) and the composition of the reaction products. Conversion, yield and selectivity were calculated as follows from the percent by weight data of the reaction products:

Conversion of TAME: $\dfrac{A - B}{A} \cdot 100 \, (\%)$

Yield of methylbutenes: $\dfrac{C \cdot [\text{TAME}]}{A \cdot [\text{methylbutene}]} \cdot 100 \, (\%)$ Selectivity of the TAME → methylbutenes reaction:

$\dfrac{C \cdot [\text{TAME}]}{(A - B) \cdot [\text{methylbutene}]} \cdot 100 \, (\%)$ In these formulae:

A = amount of TAME in the starting material
B = amount of TAME in the reaction product
C = amount of methylbutenes generated in the reaction product

[TAME] = molecular weight of TAME

[methylbutene] = molecular weight of the methylbutenes.

The water added to the reaction in Examples 6-9 has not been taken into account in the reaction product data and the calculations carried out; only the amount of water which was already contained in the starting material has been taken into account. When calculating the yield and the selectivity from the compositions, determined analytically, of the reaction products, some values of greater than 100% were computed, showing that part of the TAA present in the starting material was also dehydrated and thus led to a larger amount of methylbutenes than would have been expected from the decomposition of TAME. Only the examples with identical WHSV and identical added amounts of H$_2$O are suitable for accurate comparison. All the examples and comparison examples specified in the table were carried out at about 1 bar, a reactor temperature of 363 K. and a temperature of 393 K. of evaporated TAME or TAME/H$_2$O mixture.

In spite of the addition of H$_2$O, part of the tert.-amyl alcohol present in the starting material stream was cleaved to form methylbutene, even at relatively high WHSV.

TABLE

Cleavage of tert.-amyl methyl ether (TAME) on sulphonated styrene-divinyl-benzene resin (SPC 118) or on the same resin with SiO$_2$ doping (SPC 118/SiO$_2$),

| Reaction conditions/examples | 3 | 4 | 5 | 6 | 7 | 8 | 9 |
|---|---|---|---|---|---|---|---|
| Charge of TAME (ml/h) | 300 | 600 | 600 | 300 | 600 | 300 | 600 |
| WHSV* (g/h · ml) | 3.5 | 7 | 7 | 3.5 | 7 | 3.5 | 7 |
| Added amount of H$_2$O (ml/h) | — | — | — | 20 | 40 | 20 | 40 |
| Catalyst SPC- | 118 | 118 | 118/SiO$_2$ | 118/SiO$_2$ | 118/SiO$_2$ | 118 | 118 |
| Reaction products: all in % by weight | | | | | | | |
| 3-methylbut-1-ene | <0.1 | <0.1 | <0.1 | <0.1 | <0.1 | <0.1 | <0.1 |
| 2-methylbut-1-ene | 7.5 | 7.6 | 8.3 | 10.1 | 9.2 | 10.0 | 9.0 |
| 2-methylbut-2-ene | 51.6 | 48.5 | 52.4 | 59.1 | 55.8 | 58.2 | 55.0 |
| dimethyl ether | 0.1 | 0.1 | 0.1 | <0.1 | <0.1 | 0.1 | <0.1 |
| methanol | 26.3 | 25.4 | 26.8 | 28.0 | 28.4 | 28.1 | 28.5 |
| H$_2$O | 0.1 | 0.1 | 0.1 | 0.1 | 0.1 | 0.1 | 0.1 |
| TAME | 13.2 | 16.7 | 10.8 | 1.6 | 4.3 | 1.5 | 5.5 |
| C$_7$ ethers | 0.5 | 0.6 | 0.5 | 0.5 | 0.5 | 0.4 | 0.3 |
| tert.-amyl alcohol | <0.1 | <0.1 | <0.1 | 0.1 | 0.6 | 0.2 | 0.5 |
| C$_5$ oligomers | 0.1 | <0.1 | <0.1 | <0.1 | <0.1 | 0.4 | <0.1 |
| other hydrocarbons | 0.6 | 1.0 | 1.0 | 0.5 | 1.0 | 1.1 | 1.1 |
| Results: all in % | | | | | | | |
| Conversion  according to | 86.5 | 82.9 | 88.9 | 98.4 | 95.6 | 98.5 | 94.4 |
| Yield       the explanations | 87.9 | 83.4 | 90.3 | 102.9 | 96.7 | 101.1 | 95.2 |
| Selectivity above | 101.6 | 100.5 | 101.4 | 104.6 | 101.1 | 102.7 | 100.8 |

*WHSV = Weight Hourly Space Velocity

We claim:

1. A crosslinked organic resin, containing sulphonic acid groups, wherein said resin contains 0.1–10% by weight of SiO$_2$, relative to the total weight of the SiO$_2$-containing resin and wherein said resin is prepared by steeping the crosslinked organic resin, in the alkali form, in aqueous alkali metal silicate solution or aqueous alkylammonium silicate solution, and subsequently precipitating the SiO$_2$ using mineral acid with simultaneous conversion of the resin in to the H$^+$ form and wherein said resin is based on a sulphonated phenolformaldehyde resin, sulphonated coumarone-indene condensation product or a sulphonated styrene-divinylbenzene resin.

2. A SiO$_2$-containing resin according to claim 1 wherein said resin contains 0.3–3% by weight of SiO$_2$, relative to the total weight of the SiO$_2$-containing resins.

3. A SiO$_2$-containing resin according to claim 1, wherein the steeping and the precipitation of the SiO$_2$ is carried out repeatedly.

4. A crosslinked organic resin according to claim 1, wherein 1–20% by weight strength alkali metal silicate solution or alkylammonium silicate solution is employed.

5. A crosslinked organic resin according to claim 1, wherein the resin is allowed to swell before steeping in a polar, water-miscible organic solvent, and the steeping is carried out in the presence of this solvent, or the swelling and steeping are carried out simultaneously.

6. A crosslinked organic resin according to claim 1, wherein the steeping and precipitation steps are repeated after conversion of the resin into the alkali form.

7. A crosslinked organic resin according to claim 4, wherein 5–15% by weight strength alkali metal silicate solution or alkylammonium silicate solution is employed.

8. A cross-linked organic resin according to claim 1, wherein said resin is based on a strongly basic acidic cation exchange resin.

9. A SiO$_2$-containing resin according to claim 1, wherein the organic resin containing sulfonic acid groups is a sulfonated styrene-di-vinylbenzene resin.

* * * * *